United States Patent

Barbachyn et al.

Patent Number: 5,952,324
Date of Patent: Sep. 14, 1999

[54] BICYCLIC OXAZINE AND THIAZINE OXAZOLIDINONE ANTIBACTERIALS

[75] Inventors: Michael R. Barbachyn; Richard C. Thomas; Gary L. Cleek; Lisa M. Thomasco; Robert C. Gadwood, all of Kalamazoo, Mich.

[73] Assignee: Pharmacia & Upjohn Company, Kalamazoo, Mich.

[21] Appl. No.: 09/051,466

[22] PCT Filed: Oct. 31, 1995

[86] PCT No.: PCT/US95/12751

§ 371 Date: May 14, 1997

§ 102(e) Date: May 14, 1997

[87] PCT Pub. No.: WO96/15130

PCT Pub. Date: May 23, 1996

Related U.S. Application Data

[63] Continuation-in-part of application No. 08/339,979, Nov. 15, 1994, abandoned.

[51] Int. Cl.⁶ ..................... C07D 491/48; C07D 491/08; C07D 495/04; A61K 31/42
[52] U.S. Cl. ..................... 514/211; 514/215; 514/224.2; 514/230.5; 514/301; 514/302; 514/324; 546/114; 546/115; 540/593; 540/582; 540/477
[58] Field of Search ..................... 514/211, 215, 514/224.2, 230.5, 301, 302, 324; 546/114, 115; 540/593, 582, 477

[56] References Cited

U.S. PATENT DOCUMENTS

| | | | |
|---|---|---|---|
| 4,801,600 | 1/1989 | Wang et al. | 514/376 |
| 4,921,869 | 5/1990 | Wang et al. | 514/376 |
| 5,668,286 | 9/1997 | Yamada et al. | 546/209 |

FOREIGN PATENT DOCUMENTS

| | | |
|---|---|---|
| 0 312 000 | 10/1988 | European Pat. Off. |
| 0 316 594 | 10/1988 | European Pat. Off. |
| 0 352 781 | 7/1989 | European Pat. Off. |
| WO90/02744 | 3/1990 | WIPO |
| WO93/09103 | 5/1993 | WIPO |
| WO93/23384 | 11/1993 | WIPO |
| WO95/07271 | 3/1995 | WIPO |

OTHER PUBLICATIONS

Gregory, W.A., et al.; J. Med. Chem., 32:1673–1681 (1989).
Gregory, W.A., et al.; J. Med. Chem., 33, 2569–2578 (1990).
Park, C–H, et al.; J. Med. Chem., 35:1156–1165 (1992).
Wang, C–L, et al.; Tetrahedron, 45(5):1323–1326 (1989).

*Primary Examiner*—Richard L. Raymond
*Assistant Examiner*—Bruck Kifle
*Attorney, Agent, or Firm*—Donald L. Corneglio; Martha A. Gammill; Lucy X. Yang

[57] ABSTRACT

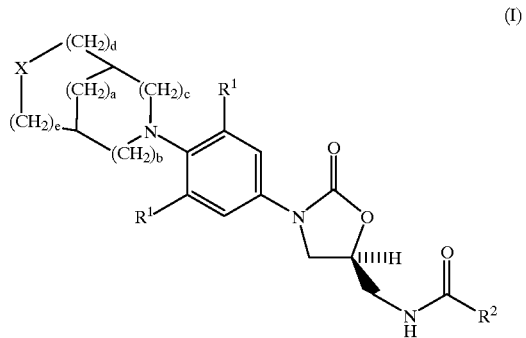

Phenyloxazolidinone compound of formula (I) or a pharmaceutically acceptable salt thereof characterized by a bicyclic thiazine or oxazine substituent. The compounds are useful antimicrobial agents, effective against a number of human and veterinary pathogens, including gram-positive aerobic bacteria such as multiply-resistant staphylococci, streptococci and enterococci as well as anaerobic organisms such as Bacteroides spp. and Clostridia spp. species, and acid-fast organisms such as *Mycobacterium tuberculosis, Mycobacterium avium* and Mycobacterium spp.

15 Claims, No Drawings

BICYCLIC OXAZINE AND THIAZINE OXAZOLIDINONE ANTIBACTERIALS

This application is the national phase of international application PCT/US95/12751, filed Oct. 31, 1995; which is a continuation-in-part of U.S. Ser. No. 08/339,979, filed Nov. 15, 1994, now abandoned.

BACKGROUND OF THE INVENTION

The subject invention discloses new and useful phenyloxazolidinone compounds characterized by having either a bicyclic thiazine or oxazine substituent. The compounds are useful antimicrobial agents, effective against a number of human and veterinary pathogens, including gram-positive aerobic bacteria such as multiply-resistant staphylococci, streptococci and enterococci as well as anaerobic organisms such as Bacteroides spp. and Clostridia spp. species, and acid-fast organisms such as *Mycobacterium tuberculosis, Mycobacterium avium* and Mycobacterium spp.

Information Disclosure

The present compounds are related by their phenyloxazolidinone ring structure to those disclosed in the publications below except that the subject compounds have either a bicyclic thiazine or oxazine phenyl substituent. The instant compounds have useful antibacterial activity.

PCT/US94/08904 application discloses oxazolidinone antibacterial compounds having either a morpholine or thiomorpholine substituent.

PCT/US93/03570 application discloses oxazolidinones containing a substituted diazine moiety and their uses as antimicrobials.

PCT/US92/08267 application discloses substituted aryl and heteroaryl-phenyl-oxazolidinones useful as antibacterial agents.

PCT/US89/03648 application discloses 5'indolinyl-5β-amidomethyloxazolidinones, 3-(fused-ring substituted) phenyl-5β-amidomethyloxazolidinones, and 3-nitrogen substituted)phenyl-5β-amidomethyloxazolidinones which are useful as antibacterial agents.

Other references disclosing various oxazolidinones include U.S. Pat. Nos. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chm.*, 35, 1156 (1992).

European Patent Publication 352,781 disclose phenyl and pyridyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

SUMMARY OF THE INVENTION

In one aspect the subject invention in a compound of structural Formula I:

Formula I

More preferred compounds, a subset of those described by structural Formula I, are represented by structural Formula II:

Formula II or pharmaceutically acceptable salts thereof wherein:
X is (a) O,
  (b) S,
  (c) SO,
  (d) $SO_2$;
$R^1$ is independently H, F, Cl or OMe;
$R^2$ is (a) hydrogen,
  (b) $C_1$–$C_8$ alkyl optionally substituted with one or more of the following: F, Cl, hydroxy, $C_1$–$C_8$ alkoxy, $C_1$–$C_8$ acyloxy,
  (c) $C_3$–$C_6$ cycloalkyl,
  (d) amino,
  (e) $C_1$–$C_8$ alkylamino,
  (f) $C_1$–$C_8$ dialkyamino,
  (g) $C_1$–$C_8$ alkoxy;
a is 0 to 3;
b is 0 to 2;
c is 0 to 2 (provided b and c cannot both be 0);
d is 0 to 2; and
e is 0 to 2 (provided d and e cannot both be 0).

In another aspect, the subject invention is directed toward a method for treating microbial infections in humans or other warm-blooded animals by administering to a patient in need thereof an effective amount of a compound of Formula I or II as described above. The compound can be administered in a pharmaceutical composition either orally, parenterally or topically. Preferably the compound is administered in an amount of from about 0.1 to about 100 mg/kg of body weight/day, more preferably, from about 3.0 to about 50 mg/kg of body weight/day.

DETAILED DESCRIPTION OF THE INVENTION

The present invention discloses novel substituted bicyclic oxazinyl- or thiazinylphenyloxazolidinones of structural Formula I and II as described above. The compounds are useful antimicrobial agents, effective against a number of human and veterinary pathogens, particularly aerobic gram-positive bacteria, including multiply-resistant staphylococci and streptococci, as well as anaerobic organisms such as bacteroides and clostridia species, and acid-fast bacteria such as as *Mycobacterium tuberculosis* and other mycobacterial species.

"Alkyl" means carbon atom chains having the designated number of carbon atoms which can be either strait chained or branched.

"Alkyl" means the designated number of carbon atoms attached to an oxygen forming such groups as methoxy (—OCH$_3$), ethyloxy, butyloxy, etc. and isomeric forms thereof.

"Acyloxy" means the designated number of carbon atoms to form an organic acid where the OH group has been deleted, such as acetyl, CH$_3$CO—; benzoyl, C$_6$H$_5$CO—.

Cycloalkyl" means the designated number of carbon atoms forming cyclopropyl, cyclobutyl, cyclopentyl, cyclohexyl, etc. and isomeric forms thereof.

"Amino" means an NH$_2$, "alkylamino" is where one of the hydrogen positions is replaced by an alkyl and "dialkylamino" is where both hydrogens are replaced by an all group.

"Pharmaceutically acceptable salts" are acid addition salts which can be prepared by any of the art recognized means. Typical, acid addition salts include hydrochloride, hydrobromide, hydrolodide, sulfate, phosphate, acetate, propionate, lactate, malate, succinate, tartrate, cyclohexanesulfamates, methanesulfonates, ethanesulfonates, benxenesulfonatess, toluenesulfonates, fumarates and other pharmaceutically acceptable couter ions for amines.

Preferably X is S.

The R$^1$ substituents are preferably both fluorine and, more preferably, fluorine and hydrogen.

The R$^2$ substituent is preferably hydrogen, methyl, dichloromethyl, hydroxymethyl or methoxy. More preferably R$^2$ is hydrogen, methoxy or methyl. It is most preferred that R$^2$ is methyl.

The preferred absolute configuration at C-5 of the oxazolidinone ring of compounds claimed in this invention is as represented in the structures of Formula I and II. This absolute configuration is called (S) under the Cahn-Ingold-Prelog nomenclature system. It is this (S)-enantiomer which is pharmacologically active. The racemic mixture is useful in the same way and for the same purpose as the pure (S)-enantiomer, the difference is that twice as much racemic material must be used to produce the same antibacterial effect. It will be apparent to one skilled in the art that when an additional chiral center(s) is present in the bicyclic oxazine or thiazine fragment of compounds of structural Formula I and II, then diastereomers are possible. Then diastereomers, in racemic and enantiomerically enriched forms, are also within the scope of the compounds of Formula I and II of the invention.

Preferred compounds of Formula I are (S)-N-[[3-[3-fluoro-4-[(1S,4S)-2-oxa-5-azabicyclo[2.2.1] heptan-5-yl]phenyl]-2-oxo-5-oxazolidinyl]methyl] acetamide (Example 1);

(S)-N-[[3-[3-fluoro-4-[1S,4S)-2-thai-5-azabicyclo[2.2.1] heptan-5-yl]phenyl]-2-oxo-5-oxazolidinyl]methyl] acetamide (Example 2);

(S)-N-[[3-[3-fluoro-4-[(1S,4S)-2-thia-2,2-dioxo-5-azabicyclo[2.2.1]heptan-5yl]phenyl]-2oxo-5-oxazolidinyl]methyl]acetamide (Example 3);

(S)-N-[[3-[3-fluoro-4-(tetrahydro-1H-thieno[3,4-c]pyrrol-5 (3H)-yl)phenyl]-2-oxo-5-oxazolidinyl]methyl]acetamide (Example 4)

(S)-N-[[3-[3-fluoro-4tetrahydro-1H-thieno[3,4-c]pyrrol-5 (3H)phenyl]-2-oxo-5-oxazolidinyl]methyl]acetamide, S-oxide (Example 5)

(S)-N-[[3-[3-fluoro-4-(tetrahydro-1H-thieno[3,4-c]pyrrol-5-(3H)yl)phenyl]-2-oxo-5-oxazolidinyl]methyl] acetamide, S,S-dioxide (Example 6)

cis-(S)-N-[[3-[3-fluoro-4-[3-oxa-7-azabicyclo[3.3.0]octane-7-yl]phenyl]-2-oxo-5-oxaaolidinyl]methyl]acetamide (Example 7)

(S)-N-[[3-[3-fluoro-4[(1R,4R)-2-thia-5-azabicyclo[2.2.1] heptan-5-yl]phenyl]2-oxo-5-oxazolidinyl]methyl] acetamide;

(S)-N-[[3-[3-fluoro-4-(2-thia-6-azabicyclo[3.2.0]heptan-6-yl)phenyl]-2-oxo-5-oxazolidinyl]methyl]acetamide;

(S)-N-[[3-[3-fluoro-4-(3-thia-6-azabicydo[3.2.0]heptan-6yl)phenyl]-2 -oxa-5-oxazolidinyl]methyl]acetamide;

(S)-N-[[3-[3-fluoro 4-(S-thia-7-azabicyclo[3.3.1]nonan-7-yl)phenyl]-2-oxa-5-oxazolidinyl]methyl]acetamide;

(S)-N-[[3-[3-fluoro-4-(3-thia-9-azabicylo[3.3.1nonan-9-yl) phenyl]-2-oxo-5-oxazolidinyl]methyl]acetamide;

(S)-N[[3-[3-fluoro-4-(2-thia-6-azabicylo[3.2.1octan-6-yl) phenyl]-2-oxo-5-oxazolidinyl]methyl]acetamide;

(S)-N-[[3-[3-fluoro-4(2-thia-6-azabicyclo[3.3.1]nonan-6-yl)phenyl]-2-oxo-5-oxazolidinyl]methyl]acetamide;

(S)-N-[[3-[3-fluoro-4-(7-thia-3-azabicyclo[4.2.1]nonan-3-yl)phenyl]-2-oxo-5-oxazolidinyl]methyl]acetamide;

(S)-N-[[3-[3-fluoro-4(9-thia-3-azabicyclo[3.3.1]nonan-3-yl)phenyl]-2-oxo-5-oxazolidinyl]methyl]acetamide;

(S)-N-[[3-[3-fluoro-4-(9-thia-3-azabicyclo[3.2.0]heptan-6-yl)phenyl]-2-oxo-5-oxazolidinyl]methyl]acetamide;

(S)-N-[[3-[3-fluoro-4 -(6-oxa-3azabicyclo[3.1.1]heptan-3-yl)phenyl]-2-oxo-5-ozazolidinyl]methyl]acetamide;

(S)-N-[[3-[3-fluoro-4-(3-oxa-7-azabicyclo[3.3.1]nonan-7-yl)phenyl]-2-oxo-5-oxzolidinyl]methyl]acetamide;

(S)-N-[[3-[3-fluoro-4-(3-oxa-9-azabicyclo[3.3.1]nonan-9-yl)phenyl]-2-oxo-5-oxalidinyl]methyl]acetamide;

(S)-N-[[3-[3-fluoro-4-(9oxa-3-azabicyclo[3.3.1]nonan-3-yl) phenyl]-2-oxo-5-oxazolidinyl]methyl]acetamide;

(S)-N-[[3-[3-fluoro-4-(2-oxa-5-azabicyclo[2.2.2]octan-5-yl)phenyl]-2-oxo-5-oxazolidinyl]methyl]acetamide;

(S)-N-[[3-[3-fluoro-4-(2-oxa-6-azabicyclo[3.2.1]octan-6-yl)phenyl]-2-oxo-5-oxalidinyl]methyl]acetamide;

(S)-N-[[3-[3-fluoro-4(3-oxa-7-azabicyclo[4.2.0]octan-7-yl) phenyl]-2-oxo-5-oxazolidinyl]methyl]acetamide;

(S)-N-[[3-[3-fluoro-4-(3-oxa-8-azabicylo[3.2.1]octan-8-yl) phenyl]-2-oxo-5-oxazolidinyl]methyl]acetamide;

(S)-N-[[3-[3-fluoro-4-(6-oxa-2-azabicyclo[3.2.1]octan-2-yl)phenyl]-2-oxo-5-oxazolidinyl]methyl]acetamide;

(s)-N-[[3-[3-fluoro-4(8oxa-3-azabicyclo[3.2.1]octan-3-yl) phenyl]-2 -oxo-5oxazolidinyl]methyl]acetamide; and (S)-N-[[3-[3-fluoro-4[(1R,4R)-2azabicyclo[2.2.1]heptan-5-yl]phenyl]-2-oxo-5-oxazolidinyl]methyl]acetamide.

The most preferred compound is (S)-N-[[3-[3-fluoro-4-[(1S,4S)-2thia-5-azabicyclo[2.2.1]heptan-5-yl]phenyl]-2-oxo-5-oxazolidinyl]methyl]acetamide (Example 2).

(S)-N-[[3-[3-fluoro-4-tetrahydro-1H-thieno[3,4-c]pyrrol-5 (3H)-yl)phenyl]-2-oxo-5-oxazolidinyl]methyl]acetamide (Example 4)

(S)-N-[[3-[3-fluoro-4-tetrahydro-1H-thieno[3,4-c]pyrrol-5-(3H)-yl)phenyl-2-oxo-5]-oxazolidinyl]methyl]acetamide, S,S-dioxide (Example 6)

The pharmaceutical compositions of this invention may be prepared by combining the compounds of Formula I or II of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems optionally contain suitable conventional coloring agents, flavoring agent stabilizers and thickening agents.

Preferably, the pharmaceutical composition is provided employing conventional techniques in unit dose form containing effective or appropriate amounts of the active component, that is, the compound of Formula I according to this invention.

The quantity of active component, that is the compound of Formula I or II according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combating, bacterial infections in warm-blooded animals, the compound or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the do may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I or II according to this invention are administered parenterally, i.e., by injection, for example, by intravenous injection or by other parenteral routes of admiration. Pharmaceutical compositions for parenteral administration will generally contain a pharmaceutically acceptable amount of the compound according to Formula I or II as a soluble salt (acid addition salt or base salt) dissolved in a pharmaceutically acceptable liquid carrier such as, for example, water-for-injection and a buffer to provide a suitably buffered isotonic solution, for example, having a pH of about 3–7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage.

The preferred method of preparation of oxazolidinones of Formula I and II in enantiomerically pure form is depicted in Charts I–IV.

As shown in Chart I, bicyclic oxazines and thiazines (commercially available or known in the literature), such as (1S,4S)-2oxa-5-azabicyclo[2.2.1]heptane (X=O) and (1S,4S)2-thia-5azabicyclo[2.2.1]heptane (X=S) of structure 1, are reacted with a functionalized nitrobenzene 2 (Y=halogen or trifluoromethanesulfonate) in the presence of a suitable base such as N,N-diisopropylethylamine and in a suitable solvent such as acetonitrile, tetrahydrofuran (THF) or ethyl acetate at ambient to reflux temperature to provide the adducts S. When X=O, the nitro group of 3 is then reduced by catalytic hydrogenation in the presence of a suitable catalyst such as 10% palladium on carbon or W-2 Raney nickel, and in a suitable solvent such as ethyl acetate, tetrahydrofuran, aqueous tetrahydrofuran, methanol and mixtures thereof, to furnish the anilines 4. In the case where X=S, the nitro group of 3 can be reduced by the action of sodium hydrosulfite in aqueous tetrahydrofuran at ambient temperature to 55° C. to give the anilines 4. Alternatively, reduction of the nitro group of 3 (X=S) can be accomplished by catalytic hydrogenation in the presence of a suitable catalyst, such as platinum on sulfide carbon or W-2 Raney nickel, and in an appropriate solvent system, for example aqueous tetrahydrofuran. The latter conditions are especially useful in that the reaction mixture is simply filtered through Celite® or the like to remove the catalyst and the filtrate containing the aniline 4 is directly used in the next step. To this end, the anilines 4 are converted to their benzyl ($R^3$=$CH_2Ph$) or methyl ($R^3$=$CH_3$) carbamate derivatives 5, employing standard Schotten-Baumann conditions or other variation known to one skilled in the art. The urethanes 5 then deprotonated with a suitable base such as n-butyllithium, lithium diisopropylamide, or lithium bis (trimethylsilyl)amide in a suitable solvent such as tetrahydrofuran or N,N-dimethylformamide and at a suitable temperature such as −78 to −60° C. to give a lithiated intermediate which is then treated with commercially available (−)-(R)-glycidyl butyrate. Warming to ambient temperature then directly affords the 5-(hydromethyl) oxazolidinones 6 in enantiomerically enriched form. Compound 6 is then converted to the corresponding mesylate 7 ($R^4$=methanesulfonyl) or aryl sulfonate 7 ($R^4$=$ArSO_2$, for example p-toluenesulfonyl) by the action of, for example, methanesulfonyl chloride/pyridine or methanesulfonyl chloride/triethylamine/dichloromethane or p-toluenesufonyl chloride/pyridine.

As illustrated in Chart II, the resultant sulfonate derivative 7 is then reacted with an azide source such as sodium or potassium azide in an aprotic solvent such as N,N-dimethylformamide (DMF) or 1-methyl-2-pyrrolidinone, optionally in the presence of a catalyst such as 18-crown-6, at a temperature of 50–90° C. to afford the aside 8. The aside is then reduced by hydrogenation with palladium on carbon or a platinum catalyst in an appropriate solvent such as ethyl acetate or methanol to give the corresponding amine 9. Alternatively, and preferably in the case where X=S, the azide can be reduced by treatment with a trivalent phosphorus compound such as triphenylphosphine in a suitable solvent such as tetrahydrofuran followed by the addition of water. Alternatively, the mesylate or aryl sulfonate group of compounds 7 can be displaced with potassium phthalimide in acetonitrile at reflux temperature to give the intermediate phthalimide 10. The phthalimide 10 is then deprotected by treatment with aqueous methyl amine in reluxing ethanol to afford the amine 9. In yet another alternative, the mesylate 7 is reacted with ammonium hydroxide in hot isopropanol or isopropanol/tetrahydrofuran, preferably in a sealed reaction vessel, to directly give the amine 9. The amino 9 is then acylated by reactions known to those skilled in the art to give oxazolidinones of structure 11. For example, the amine can be reacted with an acid chloride or anhydride in a basic solvent such as pyridine at a temperature ranging from −30 to 30° C. to provide the acylated compound 11 ($R^2$= optionally substituted alkyl). It will be apparent to one skilled in the art that other acyl groups within the scope of this invention can be readily appended to the amine 9 by standard acylation techniques, for example those highlighted in March, J. "Advanced Organic Chemistry", 4th ed.; John Wiley & Sons: New York, 1992; pp 417–425, to give additional examples of 11. The compounds of structure 11 represent examples of bicyclic oxazine- and thiazine-substituted oxazolidinone antibacterial agents of Formula II, which are the subject of this invention.

As shown in Chart III, the oxazolidinone 11, themselves examples of antibacterial agents of Formula II, can be further elaborated to additional compounds of Formula II. Specifically, 11 (X=S) can be oxidized to the corresponding sulfoxide(s) 12 (X=SO) with sodium metaperiodate in a mixture of water and methanol. It will be apparent to one skilled in the art that both endo- and exo-sulfoxides are possible, and both isomeric forms, as well as mixtures thereof, are within the scope of this invention. In addition, compounds 11 or 12 can be oxidized to the corresponding sulfones 13 ($X=SO_2$) by treatment with 4-methylmorpholine N-oxide and catalytic osmium tetroxide in aqueous acetone. It will be apparent to those skilled in the art that alternative conditions for oxidizing 11 (X=S) to 12 or 13 are known, for example those highlighted in March, J. "Advanced Organic Chemist", 4th ed.; John Wiley & Sons: New York, 1992; pp 1201–1202.

As shown in Chart IV synthesis of compounds which incorporate a thienopyrrolidine begins with reduction of the diester 14 to the diol 15 using lithium aluminum hydride as the reducing agent. Compound 15 is then converted to the bis-mesylate 16 by reaction with methanesulfonyl chloride and a trialkylamine base. Cyclization of 16 to the thienopyrrolidine 17 is carried out by reaction with sodium sulfide, and compound 17 is debenzylated to the thienopyrrole 18 by reaction with hydrogen in the presence of a suitable catalyst such as palladium on carbon. The compound of example 4 is then prepared from 18 by following the procedures outlined in Charts I and II (but substituting 18 for 1). The compounds of Examples 5 and 6 are prepared by oxidation of the compound of Example 4, using the same procedures as shown in Chart III.

Antimicrobial activity was tested in vivo using a Murine Assay procedure. Groups of female mice were injected intraperitoneally with bacteria which were thawed just prior to use and suspended in brain heart infusion with 4% Brewer's yeast UC9213 (*Staphylococcus aureus*) or brain hear infusion (Streptococcus species). Antibiotic treatment a six dose levels per drug was administered on hour and five hours after infection by either oral or subcutaneous routes. Survival was observed daily for six days. ED50 values based on mortality ratios were calculated using probit analysis. The subject compounds were compared against a well-known antibacterial (Vancomycin) as a control. The data is shown in Table 1.

TABLE 1

| In Vivo Activity Against *S. aureus* UC ® 9213 | | |
|---|---|---|
| | $ED_{50}$ (mg/kg) 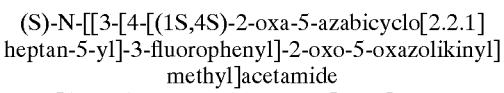 | |
| Example No. | Example, PO | Vancomycin, SC |
| 1 | 7.7 | 11.2 |
| 2 | 4.2 | 4.0 |
| 4 | 4.3 | — |
| 5 | 10.0 | — |
| 6 | 3.5 | — |

It will be apparent to those skilled in the art that the described synthetic procedures are merely representative in nature and that the use of alternative bicyclic oxazines and thiazines known in the patent and open literature allows for the preparation of additional examples of structural Formula I.

EXAMPLE 1

(S)-N-[[3-[4-[(1S,4S)-2-oxa-5-azabicyclo[2.2.1] heptan-5-yl]-3-fluorophenyl]-2-oxo-5-oxazolikinyl] methyl]acetamide Step 1: 4-[(1S,4S)-2-oxa-5-azabicyclo[2.2.1]heptan-5-yl]-3-fluoronitrobenzene A mixture of commercially available (1S,4S)-2-oxa-5-azabicyclo[2.2]heptane hydrochloride (0.200 g, 1.47 mmol), dipotassium hydrogen phosphate (1.030 g, 5.90 mmol) and 3,4-difluoronitrobenzene (0.195 mL, 1.77 mmol) in dimethyl sulfoxide (6 mL) was stirred at ambient temperature under a $N_2$ atmosphere. TLC analysis (5% $MeOH/CHCl_3$) after 3 h revealed the starting nitrobenzene was consumed. The reaction mixture was diluted with $H_2O$ and (60 mL) and extracted with $CHCl_3$. The combined organic extracts were washed with $H_2O$ and brine, dried over $Na_2SO_4$, filtered and concentrated under reduced pressure to a yellow solid. Chromatography over silica gel (60 g), eluting with a gradient of 0–2% $MeOH/CHCl_3$, afforded, after concentration of appropriate fractions, 0.314 g (90%) of the title compound as a yellow solid with mp 106.5–108° C. and MS(EI) 238 ($M^+$).

Step 2: N-(carbobenzyloxy)-4-[(1S,4S)-2-oxa-5-azabicyclo [2.2.1]heptan-5-yl]-3-fluoroaniline A solution of 4-[(1S,4S)-2-oxa-5-azabicyclo[2.2.1] heptan-5-yl]-3-fluoronitrobenzene (0.160 g, 0.672 mmol) in 3:1 $THF/H_2O$ (4 mL) was treated with acetic acid (0.115 mL) and then 10% palladium/carbon (0.020 g) under a $N_2$ stream. The atmosphere was replaced with $H_2$ (balloon) by repeated evacuation and filling and the mixture stirred at ambient temperature. After 2 h, TLC analysis (6% $CH_3CN$/ $CHCl_3$) revealed the reduction to be complete. The reaction mixture was filtered through Celite® and the filtrate immediately placed under an atmosphere of $N_2$ and treated with $K_2CO_3$ (0.464 g, 3.36 mmol) followed by benzyl chloroformate (0.117 mL, 0.864 mmol). TLC analysis (6% $CH_3CN$/ $CHCl_3$) after 0.5 h revealed the reaction to be complete. The reaction mixture was concentrated under reduced pressure and chromatographed over silica gel (20 g), eluting with a gradient of 1–5% $CH_3CN/CHCl_3$. Concentration of appropriate fractions afforded 0.226 g (98%) of the title compound as a white solid with mp 120–121° C. and MS(EI) 342 ($M^+$).

Step 3: (R)-[3-[3-[(1S,4S)-2-oxa-5-azabicyclo[2.2.1] heptan-5yl]-3-fluorophenyl]-2-oxo-5-oxazolodinyl] methanol A solution of N-(carbobenzyloxy)-4-[(1S,4S)-2-oxa-5-azabicyclo[2.2.1]heptan-5-yl]-3-fluoroaniline (0.169 g, 0.494 mmol) in dry THF (2 mL) was cooled to −78° C. under a $N_2$ atmosphere and then treated with n-butyllithium (0.312 mL of a 1.6 M solution in hexane, 0.499 mmol). After stirring 10 min at −78° C., the reaction mixture was treated with (R)-glycidyl butyrate (0.070 mL, 0.499 mmol). When the addition was completed, the cooling bath was removed and the mixture allowed to stir at ambient temperature overnight, during which time an off-white precipitate appeared . TLC analysis (5% MeOH/CHCL$_3$) revealed the reaction to be complete. The reaction mixture was treated with ca. 5 drops of saturated aqueous $NH_4Cl$, which made the reaction mixture a homogeneous solution. The reaction mixture was concentrated under reduced pressure to an off-white solid. Chromatography over silica gel, eluting with a gradient of 1–5% MeOH/CHCl$_3$, afforded, after concentration of appropriate fractions, 0.116 g (84%) of the title compound as a white solid with mp 138–140° C. and MS(EI) 308 (M$^+$). In addition, 0.018 g 10% of a second component a second component, identified as the butyrate ester of the title compound by $^1$H NMR analysis, was obtained as an amber oil.

Step 4: (R)-[[3-[4-[(1S,4S)-2-oxa-5-azabicyclo[2.2.1]heptan-5-yl]-3-fluorophenyl]-2-oxo-5-oxazolidinyl]methyl] methanesulfonate A solution of (R)-[3-[4-[(1S,4S)-2-oxa-5-azabicyclo[2.2.1]heptan-5-yl]-3-fluorophenyl]-2-oxo-5-oxazolidinyl] methanol (0.765 g, 2.48 mmol) in dry $CH_2Cl_2$ (30 mL) was cooled to 0° C. under a $N_2$ atmosphere and treated with $Et_3N$ (0.518 mL, 3.73 mmol) followed by methanesulfonyl chloride (0.202 mL, 2.61 mmol). TLC analysis (5% MEOH/CHCl$_3$) after 0.5 h revealed the reaction to be complete. The reaction mixture was washed with $H_2O$ and brine, dried over $Na_2SO_4$, filtered and concentrated in vacuo to give 0.992 g (ca. 100%) of the title compound as a tan solid. An analytical ample was prepared by recrystallization from 5% $CH_2Cl_2$/i-PrOH. This sample had mp 124.5–126° C. and MS(EI) 386 (M$^+$).

Step 5: (R)-[[3-[4-[(1S,4S)-2-oxa-5-azabicyclo[2.2.1]heptan-5-yl]-3-fluorophenyl]-2-oxo-5-oxazolidinyl]methyl] azide A solution of (R)-[[3-[4-[(1S,4S)-2-oxa-5-azabicyclo[2.2.1]heptan-5-yl]-3-fluorophenyl]-2-oxo-5-oxazolidinyl] methyl]methanesulfonate (0.869 g, 2.26 mmol) in dry DMP (10 mL) was treated with solid $NaN_3$ (0.732 g, 11.3 mmol) at ambient temperature under $N_2$. The mixture was then heated to 65° C. and reaction progress monitored by TLC. After 7.5 h at this temperature, TLC analysis (5% MeOH/CHCl$_3$) revealed the reaction to complete. The reaction mixture was diluted with EtOAc (100 mL), washed with $H_2O$ (3×15 mL) and brine, dried over $Na_2SO_4$, filtered and concentrated under reduced pressure to give 0.692 g (92%) of the title compound as a tan solid. An analytical sample was prepared by recrystallization from 1:1 EtOc/hexane as an off-white solid with mp 101–102.5° C. and MS(EI) 333 (M$^+$).

Step 6: (S)-N-[[3-[4-[(1S,4S)-2-oxa-5-azabicyclo[2.2.1]heptan-5-yl]-3-fluorophenyl]-2-oxo-5-oxazolidinyl]methyl] acetamide A solution of (R)-[[3-[4-[(1S,4S)-2-oxa-5-azabicyclo[2.2.1]heptan-5-yl]-3-fluorophenyl]-2-oxo-5-oxazolidinyl]methyl]azide (0.652 g, 1.96 mmol) in MeOH (20 mL) and $CH_2Cl_2$ (10 mL) was treated with 10% palladium/carbon (0.095 g) under a $N_2$ stream. The atmosphere was then replaced with $H_2$ (balloon) by repeated evacuation and filling and the mixture stirred at ambient temperature under $H_2$. After 3 h, TLC analysis (5% MeOH/CHCl$_3$) revealed the reduction to be complete. The reaction mixture was filtered through Celite® and the filtrate concentrated under reduced pressure. The crude 5-(aminomethyl)oxazolidinone was dissolved in $CH_2C_2$ (20 mL) and treated with pyridine (0.190 mL, 2.35 mmol) and then acetic anhydride (0.222 mL, 2.35 mmol). After 0.5 h, TLC analysis (5% MeOH/CHCl$_3$) indicated the acetylation to be complete. The reaction mixture was washed with $H_2O$ and brine, dried over $Na_2SO_4$, filtered and concentrated in vacuo to give an off-white solid. Chromatography over silica gel (70 g), eluting with a gradient of 1–3% MeOH/CHCl$_3$, afforded, after concentration of appropriate fractions, 0.517 g (76%) of the title oxazolidinone antibacterial agent as a white solid with mp 60–65° C. and MS(EI) 349 (M$^+$).

EXAMPLE 2

(S)-N-[[3-[3-fluoro-4-[(1S,4S)-2-thia-5-azabicyclo [2.2.1]heptan-5-yl]-phenyl]-2-oxo-5-oxazolidinyl] methyl]acetamide Step 1: 4-[(1S,4S)-2-thia-5-azabicyclo[2.2.1]heptan-5-yl]-fluoronitrobenzene A mixture of commercially available (1S,4S)-2-thia-5-azabicyclo[2.2.1]heptane (0.500 g, 3.30 mmol), diisopropylethylamine (1.434 mL, 8.24 mmol) and 3,4-difluoronitrobenzene (0.437 mL, 3.96 mmol) in dry acetonitrile (15 mL) was heated to reflux temperature under a $N_2$ atmosphere for 1 h and then cooled to ambient temperature overnight. The reaction mixture was concentrated under reduced pressure to give a yellow syrup. Chromatography over silica gel (50 g), eluting with chloroform, afforded, after concentration of appropriate actions, 0.700 g (84%) of the title compound as a yellow solid with mp 97–98° C. and MS(EI) 254 (M$^+$).

Step 2: (N)-(carbobenzyloxy)-4-[(1S,4S)-2-thia-5-azabicyclo[2.2.1]heptan-5-yl]-3-fluoroaniline A solution of 4-[(1S,4S)-2-thia-5-azabicyclo[2.2.1] heptan-5-yl]-3-fluoronitrobenzene (1.64 g, 6.46 mmol) in 20% $H_2O$/THF (50 mL) was treated with platinum on sulfide carbon (0.200 g) under a $N_2$ stream. The atmosphere was replaced with $H_2$ (balloon) by repeated evacuation and filling. After 12 h TLC analysis revealed a significant amount of starting material still remained. The reaction mixture was transferred to a Parr apparatus and shaken under 45 psi $H_2$. TLC analysis after 2 h indicated some string material still remained. The reaction mixture was filtered through Celite® and the filtrate, containing a mixture of the desired aniline intermediate and nitrobenzene derivative, was cooled to 0° C. and treated with $NaHCO_3$ (2.170 g, 25.8 mmol) and benzyl chloroformate (1.02 mL, 7.10 mmol). After 0.5 h the reaction mixture was concentrated under reduced pressure to a yellow/green syrup. This material was dissolved in $CHCl_3$, washed wit $H_2O$ and brine, dried over $Na_2SO_4$, filtered and concentrated in vacuo. Filtration through a plug of silica gel, eluting with 20–30% EtOAc/hexane, afforded, after concentration of appropriate fractions, a mixture of starting nitrobenzene derivative and the title compound. This material taken-up in 20% $H_2O$/THF (50 mL) and treated with W-2 Raney nickel (ca 0.400 g). The reaction mixture was shaken on a Parr apparatus under 45 psi $H_2$. After 3 h the reaction mixture was filtered through Celite® and the filtrate cooled to 0° C. and treated with $NaHCO_3$ (2.00 g, 23.8 mmol) followed by benzyl chloroformate (0.600 mL, 4.19 mmol). After 0.5 h the reaction mixture was concentrated under reduced pressure and the residue chromatographed over silica gel (125 g), eluting with 10–20% EtOAc/hexane, to afford, after concentration of appropriate fractions, 2.20 g (95%) of the title compound as a yellow solid mp 91–93° C. and MS(EI) 385 (M+).

Step 3: (R)-[3-[4-[(1S,4S)-2-thia-5-azabicyclo[2.2.1] heptan-5-yl]-3-fluorophenyl]-2-oxo-5-oxazolidinyl] methanol A solution of N-(carbobenzyloxy)-4-[(1S,4S)-2-thia-5-azabicyclo[2.2.1heptan-5-yl]-3-fluoroaniline (0.359 g, 1.00 mmol) in dry THF (4 mL) under $N_2$ was cooled to –78° C. and then treated with n-butyllithium (0.633 mL of a 1.6 M solution in hexane, 1.01 mmol). The reaction mixture was stirred at –78° C. for 15 min and then treated with (R)-glycidyl butyrate (0.151 mL, 1.00 mmol). When the addition was complete, the cooling bath was removed and the reaction mixture allowed to warm to ambient temperature overnight. TLC analysis (5% MeOH/CHCl$_3$) indicated the reaction was complete but a small amount of the butyrate ester of the title compound was present. The addition of 5 drops of a 25 wt. % solution of NaOMe/MeOH, followed by stirring for 20 min at room temperature, was effective in converting this intermediate to the title compound. The reaction mixture was treated with saturated aqueous NH$_4$Cl (10 drops) and then concentrated under reduced pressure to an oil. This material was dissolved in CH$_2$Cl$_2$ and washed with H$_2$O and brine, dried over Na$_2$SO$_4$, filtered and concentrated in vacuo to give a crude product. Chromatography over silica gel (50 g), eluting with 1–3% MeOH/CHCl$_3$, afforded, after concentration of appropriate fractions, 0.132 g (41%) of the title compound as an oil. Trituration with EtOAc afforded a precipitate, which was isolated and dried in vacuo to give an off-white solid with mp 156–157° C. and MS(EI) 324 (M+).

Step 4: (R)-[[3-[4-[(1S,4S)-2-thia-5-azabicyclo[2.2.1] heptan-5-yl]-3-fluorophenyl]-2-oxo-5-oxazolidinyl]methyl] methanesulfonate A solution of (R)-[3-[4-(1S,4S)-2-thia-5-azabicyclo [2.2.1]heptan-5-yl-3-fluorophenyl]-2-oxo-5-oxazolidinyl] methanol methanesulfonate (1.68 g, 5.19 mmol) in dry CH$_2$Cl$_2$ (100 mL) under $N_2$ was cooled to 0° C. and treated with Et$_3$N (0.793 mL, 5.70 mmol) followed by methanesulfonyl chloride (0.442 mL, 5.70 mmol). After 0.5 h at this temperature, the reaction appeared to be complete by TLC analysis (5% MeOH/CHCl$_3$). The mixture was washed with H$_2$O, saturated aqueous NaHCO$_3$ and brine, dried over Na$_2$SO$_4$, filtered and concentrated in vacuo to give 1.65 g (79%) of the title compound as a white solid with mp 139–142° C. and MS(EI) 402 (M+).

Step 5: (S)-N-[[3-[3-fluoro-4-[(1S,4S)-2-thia-5-azabicyclo [2.2.1]heptan-5-yl]-phenyl]-2-oxo-5-oxazolidinyl]methyl] acetamide A mixture of (R)[[3-[4[(1S,4S)-2-thia-5-azabicyclo [2.2.1]heptane-5-yl]-3-fluorophenyl]-2-oxo-5-oxazolidinyl] methyl]methanesulfonate (1.56 g, 3.88 mmol), 1:1 THF/i-PrOH (4 mL) and 30% NH$_4$OH (4 mL) was heated to 95° C. in a sealed tube for 14 h and then cooled to ambient temperature. TLC analysis (5% MeOH/CHCl$_3$) revealed the reaction to be complete. The mixture was diluted with CH$_2$Cl$_2$ (75 mL), washed with saturated aqueous NaHCO$_3$ (15 mL) and brine (15 mL), dried over Na$_2$SO$_4$, filtered and concentrated under reduced pressure to give a syrup. The crude 5-(aminomethyl)oxazolidinone intermediate was dissolved in CH$_2$Cl$_2$ (75 mL) and treated with pyridine (0.35 mL, 4.27 mmol) and acetic anhydride (0.403 mL, 4.27 mmol) at ambient temperature. After 1 h, TLC analysis (5% MeOH/CHCl$_3$) indicated the elation to be completed. The reaction mixture was washed with H$_2$O and brine, dried over Na$_2$SO$_4$, filtered and concentrated under reduced pressure to an amber solid. Chromatography over silica gel (125 g), eluting with 1–3% MeOH/CHCl$_3$, afforded, after concentration of appropriate fractions, 1.23 g (87%) of the title oxazolidinone antibacterial agent as a solid with mp 90–95° C. and MS(EI) 365 (M+).

EXAMPLE 3

(S)-N-[[3-[3-fluoro-4-[(1S,4S)-2-thia-2,2-dioxo-5-azabicyclo[2.2.1]heptan-5-yl]-phenyl]-2-oxo-5-oxazolidinyl]methyl]acetamide A solution of (S)-N-[[3-[3-fluoro-4[(1S,4S)-2-thia-5-azabicyclo[2.2.1]heptan-5-yl]phenyl]-2-oxo-5-oxazolidinyl]methyl]acetamide (0.300 g, 0.82 mmol) in 25% H$_2$O/acetone (16 mL) was treated at ambient temperature with 4-methylmorpholine-N-oxide (0.288 g, 2.47 mmol) followed by osmium tetroxide (0.102 mL of a 2.5 wt. % solution in tert-butanol, 0.008 mmol). After 18 h, TLC analysis (10% MOH/CHCl$_3$) revealed the oxidation was complete. The reaction was treated with saturated aqueous NaHSO$_3$ and then extracted with CHCl$_3$. The combined organic extracts were washed with brine, dried over Na$_2$SO$_4$, filtered and concentrated under reduced pressure. The residue was chromatographed over silica gel (10 g), eluting with 1–3% MEOH/CHCl$_3$, to afford, after concentration of appropriate fractions, 0.321 g (98%) of the title oxazolidinone antibacterial agent as a white solid with mp 95–105° C.

EXAMPLE 4

(S)-N-[[3-[3-fluoro-4-(tetrahydro-1H-thieno[3,4-c] pyrrol-5(3H)-yl)phenyl]-2-oxo-5-oxazolidinyl] methyl]acetamide Step 1: cis-1-(Phenylmethyl)-3,4-pyrrolidinedimethanol (cis)-1(Phenylmethyl)-3,4-pyrrolidinedicarboxylic acid, dimethyl ester was prepared according to the procedure of Y. Terao, et al (*Chem. Pharm. Bull.*, 1985, 33, 2762–66). To a stirred solution of this diester (12.14 g, 43.8 mmol) in dry THF (175 mL) under $N_2$ cooled to 0° C. was added dropwise a solution of lithium aluminum hydride (1M in THF, 87 mL, 87 mmol) over 15 min. The reaction mixture was stirred at 0° C. for 1 h, then at RT for 18 h. The reaction mixture was cooled to 0° C. and quenched with successive addition of H$_2$O (3.2 mL), 5 N NaOH (3.2 mL) and H$_2$O (11.7 mL). The reaction mixture became very thick and stirring was difficult. The reaction mixture was diluted with ether (500 mL) and filtered through a small pad of celite. The filter cake was washed with ether (250 mL). The filtrate was washed with H$_2$O (1×800 mL) and the organics were dried (MgSO$_4$), filtered and concentrated to afford 9.3 g (41.8 mmol, 96%) of the desired diol and a thick yellow oil. Used without further purification. HRMS (FAB) calcd for C$_{13}$H$_{19}$NO$_2$+H 222.1494, found 222.1490.

Step 2: cis-1-(Phenylmethyl)-3,4-di(methylsulfonyloxy) methylpyrrolidine

To a stirred solution of cis-1-(phenylmethyl)-3,4-pyrrolidinedimethanol (9.2 g, 41.6 mmol) in CH$_2$Cl$_2$ (240 mL) cooled to 0° C. was added triethylamine (29 mL, 208.1 mmol) followed by methanesulfonyl chloride (8.1 mL, 104.0 mmol). The reaction mixture was stirred at 0° C. for 15 min, then at RT for 1.5 h. The reaction mixture was poured into H$_2$O (240 mL) and the phases were separated. The aqueous phase was extracted with CH$_2$Cl$_2$ (1×100 mL). The combined organics were dried (MgSO$_4$), filtered and concentrated. The residue was purified by flash chromatography using ethyl acetate as the eluent to afford 14.2 g (37.5 mmol, 90%) of the desired bis-mesylate as a thick yellow oil. HRMS (EI) calcd for $C_{15}H_{23}NO_6S_2$ 377.0967, found 377.0958.

Step 3: Hexahydro-5-(phenylmethyl)-1H-thieno[3,4-c]pyrrole

To a stirred solution of cis-1-(phenylmethyl)-3,4-di(methylsulfonyloxy)methylpyrrolidine (9.2 g, mmol), in dry DMSO (48 mL) was added anhydrous sodium sulfide (5.7 g, 73.3 mmol). The dark reaction mixture was heated at 120° C. for 18 h. The cooled reaction mixture was poured into ice $H_2O$ (150 mL). The resulting mixture was washed with ether (3×200 mL). The combined organics were dried ($MgSO_4$), filtered and concentrated. The resulting residue was purified by flash chromatography using ethyl acetate as the eluent to afford 4.2 g (19.1 mmol, 78%) of the desired product as a thick yellow oil. HRMS (EI) calcd for $C_{13}H_{17}NS$ 219.1082, found 219.1080. Anal. calcd for $C_{13}H_{17}NS$: C, 71.19; H, 7.81; N, 6.39. Found: C, 70.82; H, 7.83; N, 6.35.

Step 4: Hexahydro-1H-theino[3,4-c]pyrrole, hydrochloride

To a stirred solution of hexahydro-5-phenylmethyl)1H-thieno[3,4-c]pyrrole (1.2 g, 5.3 mmol) in $CH_2Cl_2$ (21 mL) cooled to 0° C. was added dropwise via syringe 1-chloroethylchloroformate (1.15 mL, 10.7 mmol). The reaction mixture was stirred at 0° C. for 20 min, then at RT for 90 min. The reaction mixture was concentrated. The resulting residue was purified by flash chromatography using 25% ethyl acetate in hexane as the eluent to afford 611.3 mg (2.6 mmol, 49%) of 1-chloroethylcarbamate. The column was then washed with 20% methanolic ammonia in $CHCl_3$ a to afford 160.5 mg (1.24 mmol, 23%) of desired amine as the free base. The 1-chloroethylcarbamate (611.3 mg, 2.6 mmol) was dissolved in methanol (15 mL) and heated at reflux for 90 min. The cooled reaction mixture concentrated to afford 408.0 mg (2.5 mmol, 47%) of the desired amine as the HCl Salt (based on chlorocarbamate). mp 149–151° C.; HRMS (EI) calcd for $C_6H_{,11}$, NS 129.0612, found 129.0614. Anal. Calcd for $C_6H_{12}CINS$: C, 43.50; H, 7.30; N, 8.45; Cl: 21.39; S: 19.35. Found: C, 43.39; H, 7.28; N, 8.24; Cl: 21.08; S: 19.12.

Step 5: 5-(2-Fluoro-4nitrophenyl)-hexahydro-1H-thieno[3,4-c]pyrrole

To a stirred suspension of hexahydro-5-1H-thieno[3,4-c]pyrrole, hydrochloride (147.3 mg, 0.89 mmol) in acetonitrile (5 mL) was added 3,4-fluoronitrobenzene (0.11 mL, 0.98 mmol) followed by diisopropylethyl amine (0.36 mL, 2.05 mmol). The homogeneous reaction mix was heated at reflux for 18 h. The cooled reaction mixture was concentrated. The resulting residue was diluted with EtOAc (50 mL) and washed with saturated aqueous $NH_4Cl$ (1×25 mL). The aqueous layer was extracted with EtOAc (1×30 mL). Combined organics were washed with saturated $NaHCO_3$ (1×40 mL), brine (1×40 mL), dried ($MgSO_4$), filtered and concentrated. The residue was purified by flash chromatography using 20% EtOAc in hexane as the eluent to afford 202.5 mg (0.75 mmol, 89%) of the desired nitro compound as a bright yellow solid. mp 107–109° C.; Anal. calcd for $C_{12}H_{13}FN_2O_2S$: C, 53.72; H, 4.88; N, 10.44; S: 11.95. Found: C, 53.38; H, 5.03; N, 10.34; S: 11.89.

Step 6: 3-[3-fluoro-4-(tetrahydro-1H-thieno[3,4-c]pyrrol-5(3H)-yl)phenylcarbamic acid, phenylmethylester To a stirred solution of 5-(2-fluoro-4-nitrophenyl)-hexahydro-1H-thieno[3,4-c]pyrrole (1.44 g, 5.4 mmol) in ethanol (70 mL) was added 2 M aqueous $CuSO_4$ (2.9 mL). This mixture was cooled to 0° C. and odium borohydride (1.10 g, 26.8 mmol) was added portionwise. (Caution: Very exothermic!) The dark reaction mixture was then heated at reflux for 2 h. The cooled reaction mixture was partitioned between EtOAc and $H_2O$. The phases were separated. The aqueous phase was extracted with EtOAc (3×100 ml). The combined organics were dried ($MgSO_4$), filtered and concentrated. The resulting dark residue was dissolved in acetone/$H_2O$ (2:1, 60 mL). This stirred solution was cooled to 0° C. and solid $NaHCO_3$ (1.35 g, 16.1 mmol) was added followed by beneylchloroformate (1.9 mL, 13.4 mmol). The reaction mixture was stirred at 0° C. for 15 min, then at RT for 2 h. The reaction mixture was quenched by cares addition of 10% aqueous $NaHSO_4$ (30 mL). The reaction mixture was poured into EtOAc (250 mL) and the phases were separated. The aqueous layer was extracted with EtOAc (1×100 mL). The combined organic layers were dried ($MgSO_4$), filtered and concentrated. The residue was purified by flash chromatography using 20% EtOAc in hexane to afford 1.6 g (4.3 mmol, 81%) of the desired carbamate: mp 101–102° C.; Anal. Calcd for $C_{20}H_{21}FN_2O_2S$: C, 64.50; H, 5.68; N, 7.52; S: 8.61. Found: C, 64.33; H, 5.56; N, 7.53; S: 8.61.

Step 7: (5R)-3-[3-Fluoro-4-(tetrahydro-1H-thieno[3,4-c]pyrrol-5-(3H)-yl)phenyl]-5-(hydroxymethyl)-2-oxazolidinone To a stirred solution of 3-[3-fluoro-4-(tetrahydro-1H-thieno-3,4-c]pyrrol-5-(3H)-yl)phenylcarbamic acid, phenylmethyl ester (1.86 g, 3.6 mmol) dry THF (14 mL) under $N_2$ cooled to −78° C. was added n-butylithium (1.6 M in hexane, 2.4 mL, 3.8 mmol). The reaction mixture was stirred at −78° C. for 35 min and then R-(−)-glycidylbutyrate (0.54 mL, 3.8 mmol) was added. The reaction mixture was stirred at −78° C. for 30 min, then at RT overnight. A thick precipitate had formed. The reaction mixture was quenched with saturated aqueous $NH_4Cl$ (14 mL) and poured into EtOAc (50 mL). The phases were separated. The organic layer was washed with saturated aqueous $NaHCO_3$ (1×30 mL), brine (1×30 mL), dried ($MgSO_4$), filtered and concentrated. The residue was purified by flash chromatography using EtOAc as the eluent to afford 801.6 mg (2.4 mmol, 65%) of the desired product. mp 165–167° C.; Anal. Calcd for $C_{16}H_{19}FN_2O_3S$: C, 56.79; H, 5.66; N, 8.28; S: 9.48. Found: C, 56.88; H, 5.74; N, 8.21; S: 9.33.

Step 8: (5R)-3-[3-Fluoro-4-tetrahydro-1H-thieno[3,4-c]pyrrol-5(3H)-yl)phenyl]-5-[[(methylsufonyl)oxy]methyl]-2-oxazolidinone To a stirred solution (5R)-3-fluoro-4-(tetrahydro-1H-thieno[3,4-c]pyrrol-5(3H)-yl)phenyl]-5-(hydroxymethyl)-2-oxazolidinone (656.5 mg, 1.9 mmol) in $CH_2Cl_2$ (20 mL) cooled to 0° C. was added triethylamine (0.41 mL, 2.9 mmol) followed by methanesulfonylchloride (0.18 mL, 2.3 mmol). The reaction mixture was stirred at 0° C. for 15 min, then at RT for 18 h. The reaction mixture was poured into $H_2O$ (20 mL). the phase was separated. The aqueous layer was extracted with $CH_2Cl_2$ (1×50 mL). The combined organic layer were dried ($MgSO_4$), filtered and concentrated the residue was triturated with ether/hexane and solid was isolated by filtration and dried to afford 773.9 mg (1.9 mmol, 96%) of the desired mesylate. mp 148–150° C.; Anal. Calcd for $C_{17}H_{21}FN_2O_5S_2$: C, 49.03; H, 5.08; N, 6.73; S: 15.40. Found: C, 48.56; H, 5.12; N, 6.48; S: 15.41. Found: C, 48.46; H, 5.25; N, 6.38.

Step 9: (S)-N-[[3-[3-fluoro-4-tetrahydro-1H-thieno[3,4-c]pyrrol-5(3H)-yl)phenyl]-2-oxo-5-oxazolidinyl]methyl]acetamide A stirred suspension of (5R)-3-[3-fluoro-4-(tetrahydro)-1H-thieno[3,4-c]pyrrol-5(3H)-yl)phenyl]-5-[[(methylsufonyl)oxy]methyl]-2-oxazolidinyl (208.5 mg, 0.5 mmol) in THF (3 mL) and methanolic ammonia (3 mL) was heated in a sealed tube at 100° C. for 48 h. (The reaction mixture became homogenous at about 80° C.) The cooled reaction mixture was concentrated and the resulting residue was dissolved in $CH_2Cl_2$ (5 mL) and cooled to 0° C. To this stirred suspension was added pyridine (0.12 mL, 1.5 mmol) followed by acetic anhydride (60 μL, 0.6 mmol). The homogeneous reaction mixture was at 0° C. for 15 min, then at RT for 1 h then concentrated. The residue was purified by flash chromatography using 7% methanol in EtOAc an the eluent to afford 148.2 mg (0.4 mmol, 78%) of the desired acetamide. mp 143–144° C.; $KF-H_2O$: 0.52% Anal. Calcd for $C_{18}H_{22}FN_3O_3S$ plus 0.52% $H_2O$: C, 56.68; H, 5.87; N, 11.01; S: 8.40. Found: C, 56.31; H, 5.90; N, 10.74; S: 8.30.

EXAMPLE 5

(S)-N-[[3-[3-fluoro-4-(tetrahydro-1H-thieno[3,4-c]pyrrol-5(3H)-yl)phenyl]-2-oxo-5-oxazolidinyl]methyl]acetamide, S-oxide To a stirred solution of (S)-N-[[3-[3-fluoro-4-(tetrahydro-1H-thieno[3,4-c]pyrrol-5(3H)-yl)phenyl]-2-oxo-5-oxazolidinyl]methyl]acetamide (216.8 mg, 0.57 mmol) in methanol (4 mL) and $H_2O$ (4 mL) cooled to 0° C. was added sodium metaperiodate (134.4 mg, 0.63 mmol). The reaction mixture was stirred at 0° C. for 1 h, then at RT for 18 h. The solid precipitation was removed by filtration. The solid was washed with $CHCl_3$ (50 mL). The filtrate was washed with $H_2O$ (1×30 ml). The aqueous layer was extracted with $CHCl_8$ (2×25 mL). The combined organic layers were dried ($MgSO_4$), filtered and concentrated. The residue was purified by flash chromatography using 7% methanol in $CH_2Cl_2$ as the eluent to afford 195.7 mg (0.5 mmol, 87%) of the desired sulfoxide. mp 162–164° C.; HRMS (EI) calcd for $C_{18}H_{22}FN_3O_4S$ 395.1315, found 395.1309. $KF-H_2O$: 2.87% Anal. Calcd for $C_{18}H_{22}FN_3O_4S$ plus 2.87% $H_2O$: C, 53.09; H, 5.76; N, 10.32; S: 7.87. Found: C, 53.07; H, 6.01; N, 10.20; S: 7.87.

EXAMPLE 6

(S)-N-[[3-[3-fluoro-4-(tetrahydro-1H-thieno[3,4-c]pyrrol-5(3H)-yl)phenyl]-2-oxo-5-oxazolidinyl]methyl]acetamide, S,S-dioxide To a stirred solution of (S)-N-[[3-[3-fluoro-1H-thieno[3,4-c]pyrrol-5(3H)-yl)phenyl]-2-oxo-5-oxazolidinyl]methyl]acetamide (213.9 mg, 0.56 mmol) in 25% acetone/$H_2O$ (8 mL) was added N-methylmorpholine-N-oxide (198.1 mg, 1.7 mmol) followed by osmium tetroxide in tert-butanol (2.5% by wt.) (30 μL, 0.08 mmol). The reaction mixture was stirred at RT for 18 h. The reaction mixture was quenched by careful addition of saturated sodium bisulfite (8 mL). The mixture was poured into $CH_2Cl_2$ (50 mL) and the phases were separated. The aqueous phase was extracted with $CH_2Cl_2$ (2×25 mL). The combined organic layers were washed with brine (1×30 mL), dried ($MgSO_4$), filtered and concentrated. The residue was purified by flash chromatography using 7% methanol in $CHCl_3$ as the eluent to afford 194.3 mg (0.47 mmol, 84%) of desired sulfone. mp 135–137° C.; HRMS (EI) calcd for $C_{18}H_{22}FN_3O_5S$ 411.1264, found 411.1263. $KF-H_2O$: 1.10%. Anal Calcd for $C_{18}H_{22}FN_3O_5S$ plus 1.10% $H_2O$: C, 51.96; H, 5.45 N, 10.10; S, 7.71. Found: C, 51.73; H, 5.62; N, 9.96; S: 7.75.

EXAMPLE 7 cis-(S)-N-[[3-[3-fluoro-4-[oxa-7-azabicyclo[3.3.0]octane-7-yl]phenyl]-2-oxo-5-oxazolidinyl]methyl]acetamide Following the general procedure of EXAMPLE 2 and making noncritical variations but substituting hexahydro-1H-furo(3,4-c)pyrrole (Miller, A. D. U.S. Pat. No. 3,975,532 1976). (2.33 g, 20.66 mmol) for (1S,4S)-2-thia-5-azabicyclo[2.2.1]heptane, compound is obtained, mp 124–126°C.

Chart I

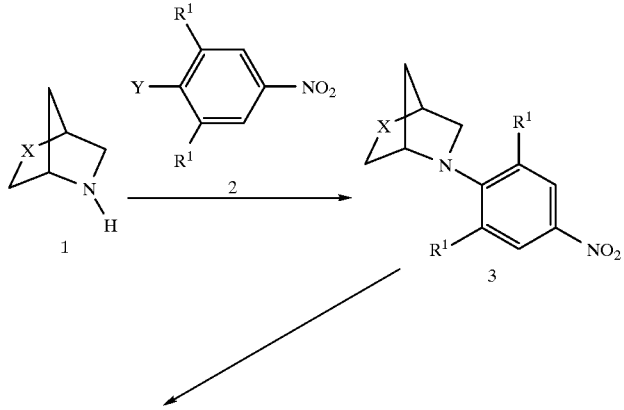

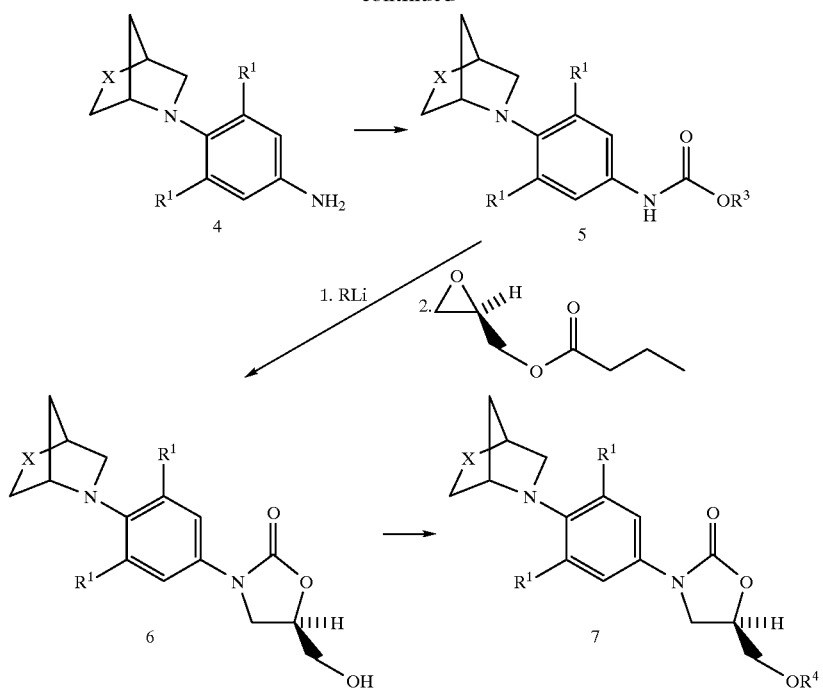
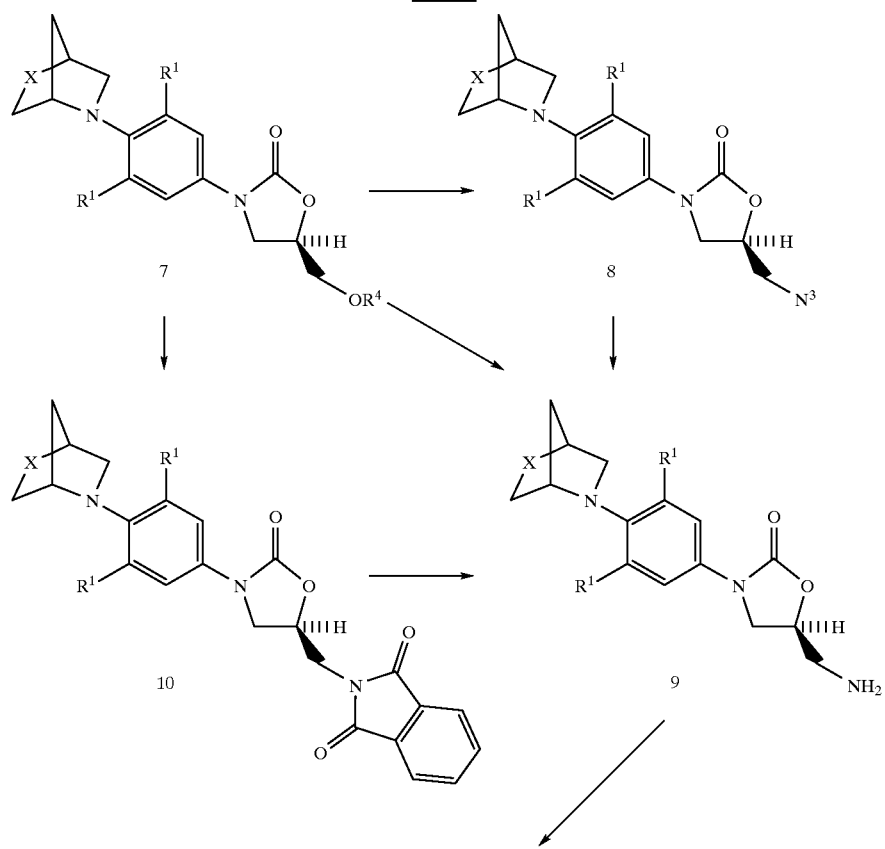
Chart II

-continued
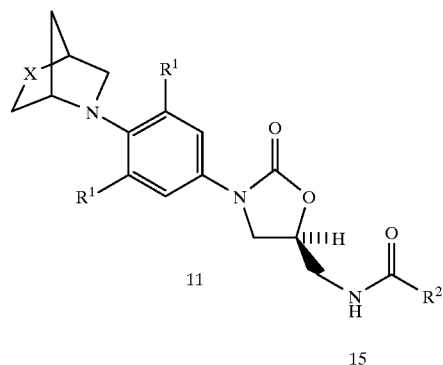
Chart III
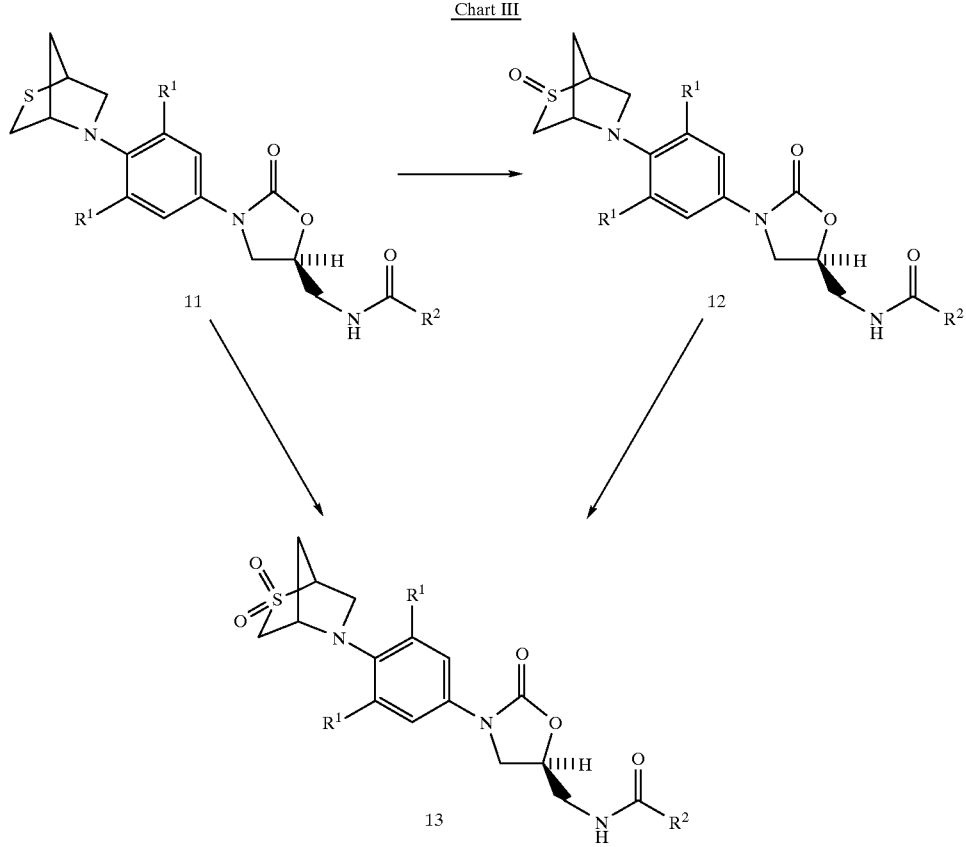
Chart IV
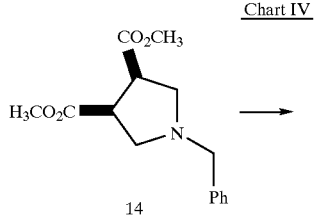
-continued
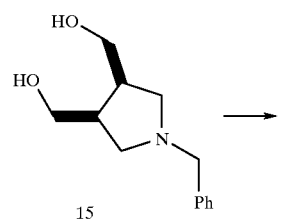

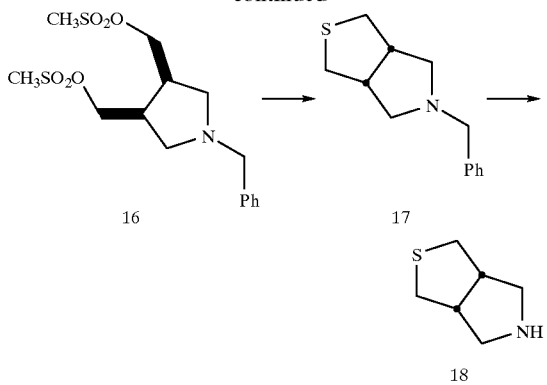

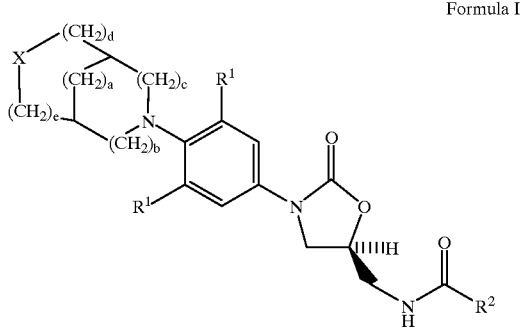

What is claimed:
1. A compound of structural Formula I:

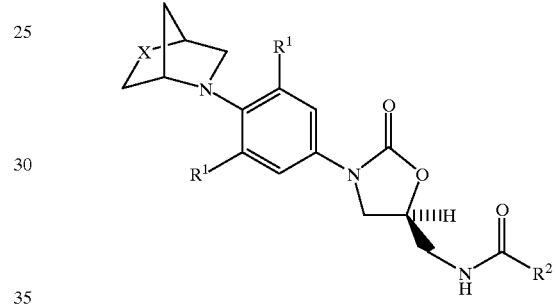

Formula I or a pharmaceutically acceptable Salt thereof wherein:
X is (a) O,
(b) S,
(c) SO,
(d) $SO_2$;
$R^1$ is independently H, F, Cl or OMe;
$R^2$ is (a) hydrogen,
(b) $C_1$–$C_8$ alkyl optionally substituted with one or more of the following: F, Cl, hydroxy, $C_1$–$C_8$ alkoxy, $C_1$–$C_8$ acyloxy,
(c) $C_3$–$C_6$ cycloalkyl,
(d) amino,
(e) $C_1$–$C_8$ alkylamino,
(f) $C_1$–$C_8$ dialkylamino,
(g) $C_1$–$C_8$ alkoxy;
a is 0 to 3; b is 0 to 2; c is 0 to 2 (provided b and c cannot both be 0); d is 0 to 2;
and e is 0 to 2 (provided d and e cannot both be 0).
2. The compound of claim 1 wherein X is S.
3. The compound of claim 1 wherein each $R^1$ is independently H or F.
4. The compound of claim 3 wherein each $R^1$ is F.
5. The compound of claim 1 wherein $R^2$ is hydrogen, a $C_1$–$C_8$ alkoxy, or a $C_1$–$C_8$ alkyl optionally substituted with one or more Cl or OH.

6. The compound of claim 1 wherein $R^2$ is methyl, dichloromethyl, hydroxymethyl, or methyl.
7. The compound of claim 1 which is:
a) (S)-N-[[3-[3-fluoro-4-[(1S,4S)-2-oxa-5-azabicylo[2.2.1]heptan-5-yl]phenyl]-2-oxo-5-oxazolidinyl]methyl]acetamide;
b) (S)-N-[[3-[3-fluoro-4-[(1S,4S)-2-thia-5-azabicyclo[2.2.1]heptan-5-yl]phenyl]-2-oxo-5-oxazolidinyl]methyl]acetamide; or
c) (S)-N-[[3-[3-fluoro-4-[(1S,4S)-2-thia-2,2-dioxo-5-azabicyclo-[2.2.1]heptan-5-yl]phenyl]-2-oxo-5-oxalidinyl]methyl]acetamide.
8. The compound of claim 1 which is the S-enantiomer form.
9. The compound of claim 1 wherein c and b are both 1.
10. The compound of claim 9 wherein d and e are both 1.
11. The compound of claim 10 wherein a is 0.
12. A method for treating microbial infections in a patient in need thereof by administering an effective amount of a compound of Formula I.
13. A compound of structural Formula II:

Formula II or pharmaceutically acceptable salts thereof wherein:
X is (a) O,
(b) S,
(c) SO,
(d) $SO_2$;
$R^1$ is independently H, F, Cl or OMe; and
$R^2$ is (a) hydrogen,
(b) $C_1$–$C_8$ alkyl optionally substituted with one or more of the following: F, Cl, hydroxy, $C_1$–$C_8$ alkoxy, $C_1$–$C_8$ acyloxy,
(c) $C_3$–$C_6$ cycloalkyl,
(d) amino,
(e) $C_1$–$C_8$ alkylamino,
(f) $C_1$–$C_8$ dialkylamino,
(g) $C_1$–$C_8$ alkoxy.
14. The compound of claim 13 which is the S-enantiomer form.
15. A method for treating microbial infections in warm-blooded animals by administering to a patient in need thereof an effective amount of a compound of Formula II.

* * * * *